United States Patent
Nowakowski et al.

(10) Patent No.: US 6,998,483 B2
(45) Date of Patent: Feb. 14, 2006

(54) PROCESS FOR THE PREPARATION OF SULPHONAMIDE-SUBSTITUTED IMIDAZOTRIAZINONES

(75) Inventors: Marc Nowakowski, Wuppertal (DE); Reinhold Gehring, Wuppertal (DE); Werner Heilmann, Wuppertal (DE); Karl-Heinz Wahl, Odenthal (DE)

(73) Assignee: Bayer HealthCare Aktiengesellschaft, Leverkusen (DE)

( * ) Notice: Subject to any disclaimer, the term of this patent is extended or adjusted under 35 U.S.C. 154(b) by 0 days.

(21) Appl. No.: 11/124,452

(22) Filed: May 5, 2005

(65) Prior Publication Data
US 2005/0203298 A1  Sep. 15, 2005

Related U.S. Application Data

(63) Continuation of application No. 10/884,686, filed on Jul. 2, 2004, now abandoned, which is a continuation of application No. 10/022,954, filed on Dec. 17, 2001, now Pat. No. 6,777,551.

(30) Foreign Application Priority Data
Dec. 18, 2000  (DE) .................. 100 63 108

(51) Int. Cl.
*C07D 487/04* (2006.01)
(52) U.S. Cl. ........................ 544/184; 544/112
(58) Field of Classification Search .......... 544/184
See application file for complete search history.

(56) References Cited

U.S. PATENT DOCUMENTS 6,362,178 B1  3/2002  Niewohner et al. ......... 514/218

FOREIGN PATENT DOCUMENTS

WO  9924433  5/1999

WO  WO 200264593 A1 *  8/2002

* cited by examiner

*Primary Examiner*—Venkataraman Balasubramanian
(74) *Attorney, Agent, or Firm*—Susan M. Pellegrino

(57) ABSTRACT

The present invention relates to a process for the preparation of sulphonamide-substituted imidazotriazinones of the general formula (I)

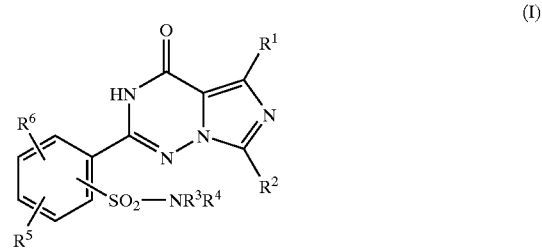

characterized in that compounds of the formula (II)

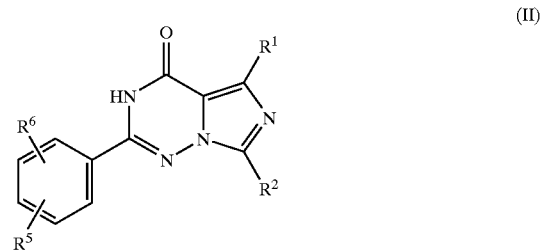

are reacted with sulphuric acid and the products obtained are then reacted with thionyl chloride and converted in situ in an inert solvent using an amine into the compounds according to the invention and, if appropriate, reacted to give the corresponding salts, hydrates or N-oxides.

1 Claim, No Drawings

PROCESS FOR THE PREPARATION OF SULPHONAMIDE-SUBSTITUTED IMIDAZOTRIAZINONES

This application is a continuing application of U.S. Ser. No. 10/884,686, filed Jul. 2, 2004, now abandoned, which is a continuing application of U.S. Ser. No. 10/022,954, filed Dec. 17, 2001 now U.S. Pat. No. 6,777,551.

The present invention relates to a process for the preparation of sulphonamide-substituted imidazotriazinones.

It is known that compounds which are able to inhibit cyclic guanosine 3',5'-monophosphate-metabolizing phosphodiesterases (cGMP PDEs) can be employed for the treatment of impotence (cf., for example, EP-B 0 702 555; K. Murray, Drugs, News & Perspectives 6 (1993), 150).

In WO 99/24433, sulphonamide-substituted imidazotriazinones are described as potent inhibitors of either one or more of the cyclic guanosine 3',5'-monophosphate-metabolizing phosphodiesterases (cGMP PDEs). According to the nomenclature of Beavo and Reifsnyder (Trends in Pharmacol. Sci. 11, 150–155, 1990), these cGMP PDEs are the phosphodiesterase isoenzymes PDE-I, PDE-II and PDE-V.

According to WO 99/24433, the sulphonamide-substituted imidazotriazinones described therein are prepared from corresponding 2-ethoxyphenyl-substituted imidazotriazinones by reaction with chlorosulphonic acid and subsequent reaction with an appropriate amine, as is illustrated by the following scheme ($R^1$ to $R^6$ here have the meanings indicated in WO 99/24433):

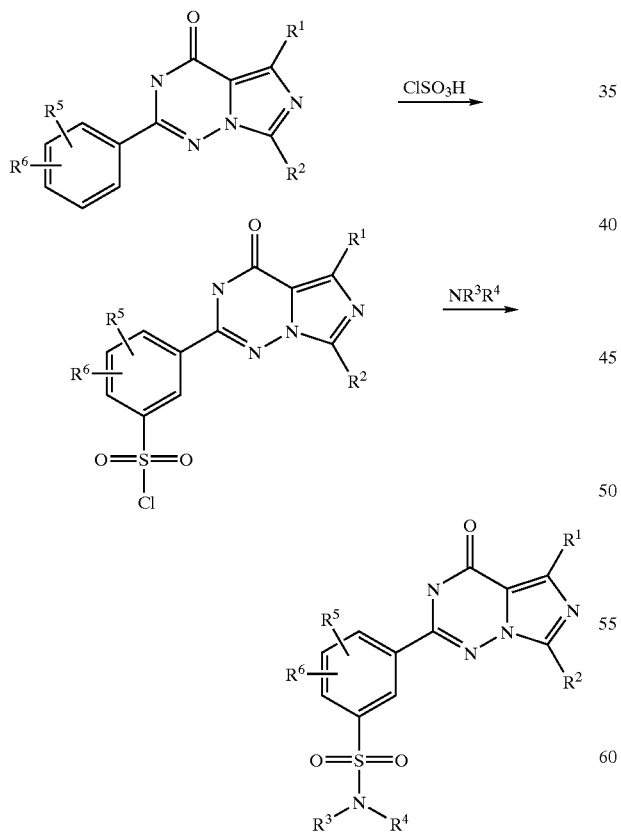

In this process, highly reactive chlorosulphonic acid has to be used as a reagent. Moreover, the imidazotriazinone-sulphonyl chlorides formed as intermediates are sensitive to hydrolysis, which, in particular in the conversion of this preparation process to the industrial scale, can lead to not inconsiderable yield variations.

It was therefore the object of the present invention to make available a process for the preparation of sulphonamide-substituted imidazotriazinones in which the disadvantages of the above process known from the prior art are avoided.

This object is achieved according to the present invention by a process as in claim 1. In particular, in the process according to the invention as in claim 1 the use of chlorosulphonic acid is avoided by introduction of the sulphonic acid via a reaction with sulphuric acid and subsequent reaction with thionyl chloride. Moreover, the reaction with thionyl chloride and the subsequent reaction with an amine is carried out in a one-pot process, so that the imidazotriazinonesulphonyl chloride intermediate, which is sensitive to hydrolysis, does not need to be isolated. By means of this, yield variations on account of partial hydrolysis of this intermediate can be excluded. As a result of these advantages, the process according to the invention is much simpler to carry out on the industrial scale than the process described in WO 99/24433.

The process according to the invention comprises the preparation of compounds of the formula (I)

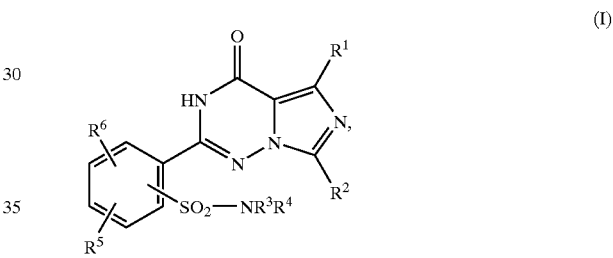

in which
$R^1$ represents hydrogen or straight-chain or branched alkyl having up to 4 carbon atoms,
$R^2$ represents straight-chain alkyl having up to 4 carbon atoms,
$R^3$ and $R^4$ are identical or different and represent a straight-chain or branched alkyl chain having up to 5 carbon atoms, which is optionally substituted up to two times in an identical or different manner by hydroxyl or methoxy, or
$R^3$ and $R^4$, together with the nitrogen atom, form a piperidinyl, morpholinyl or thiomorpholinyl ring or a radical of the formula

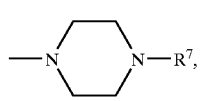

in which
$R^7$ denotes hydrogen, formyl, straight-chain or branched acyl or alkoxycarbonyl each having up to 6 carbon atoms, or straight-chain or branched alkyl having up to 6 carbon atoms, which is optionally mono- to disubstituted, in an identical or different manner, by hydroxyl, carboxyl, straight-chain or branched alkoxy or alkoxycarbonyl each having up to 6 carbon atoms, or denotes $C_{3-8}$-cycloalkyl, and the heterocycles mentioned under $R^3$ and $R^4$, formed together with the nitrogen atom, are optionally mono- to disubstituted, in an identical or different manner, if appropriate also geminally, by hydroxyl, formyl, carboxyl, straight-chain or branched acyl or alkoxycarbonyl each having up to 6 carbon atoms, and/or the heterocycles mentioned under $R^3$ and $R^4$, formed together with the nitrogen atom, are optionally substituted by straight-chain or branched alkyl having up to 6 carbon atoms, which is optionally mono- to disubstituted, in an identical or different manner, by hydroxyl or carboxyl, and/or the heterocycles mentioned under $R^3$ and $R^4$, formed together with the nitrogen atom, are optionally substituted by piperidinyl or pyrrolidinyl linked via N, $R^5$ and $R^6$ are identical or different and represent hydrogen, straight-chain or branched alkyl having up to 6 carbon atoms, hydroxyl or straight-chain or branched alkoxy having up to 6 carbon atoms, characterized in that compounds of the formula (II)

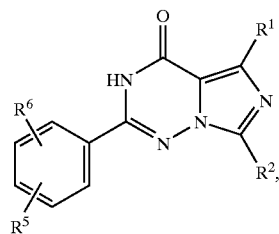

(II)

in which
$R^1$, $R^2$, $R^5$ and $R^6$ have the meanings indicated above, are reacted with sulphuric acid to give compounds of the formula (III)

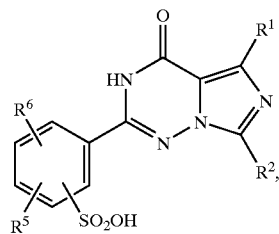

(III)

in which
$R^1$, $R^2$, $R^5$ and $R^6$ have the meanings indicated above, and then with thionyl chloride and the product thus obtained is reacted in situ in an inert solvent with an amine of the formula (IV)

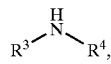

(IV)

in which
$R^3$ and $R^4$ have the meaning indicated above, and, if appropriate, reacted to give the corresponding salts, hydrates or N-oxides.

According to a preferred embodiment of the present invention, in the case of the reactants and the final product of the process according to the invention $R^1$ denotes hydrogen or straight-chain or branched alkyl having up to 4 carbon atoms, $R^2$ denotes straight-chain alkyl having up to 4 carbon atoms, $R^3$ and $R^4$ identically to or differently from one another denote a straight-chain or branched alkyl chain having up to 5 carbon atoms, which is optionally substituted up to two times in an identical or different manner by hydroxyl or methoxy, or $R^3$ and $R^4$, together with the nitrogen atom, form a piperidinyl or morpholinyl ring or a radical of the formula

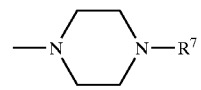

in which
$R^7$ denotes hydrogen, straight-chain or branched alkyl having up to 4 carbon atoms, which is optionally mono- or disubstituted, in an identical or different manner, by hydroxyl, straight-chain or branched alkoxy each having up to 4 carbon atoms, or denotes $C_{3-6}$-cycloalkyl, and the heterocycles mentioned under $R^3$ and $R^4$, formed together with the nitrogen atom, are optionally mono- or disubstituted, in an identical or different manner, if appropriate also geminally, by hydroxyl, straight-chain or branched acyl or alkoxycarbonyl each having up to 4 carbon atoms, optionally by straight-chain or branched alkyl having up to 4 carbon atoms, which is optionally mono- or disubstituted, in an identical or different manner, by hydroxyl, $R^5$ and $R^6$ identically to or differently from one another denote hydrogen, straight-chain or branched alkyl having up to 6 carbon atoms, hydroxyl or straight-chain or branched alkoxy having up to 6 carbon atoms.

According to a particularly preferred embodiment of the present invention, in the case of the reactants and the final product of the process according to the invention $R^1$ denotes hydrogen or straight-chain or branched alkyl having up to 4 carbon atoms, $R^2$ denotes straight-chain alkyl having up to 4 carbon atoms, $R^3$ and $R^4$ identically to or differently from one another denote methyl or ethyl, which are optionally substituted up to two times in an identical or different manner by hydroxyl, or $R^3$ and $R^4$, together with the nitrogen atom, form a piperidinyl or morpholinyl ring or a radical of the formula

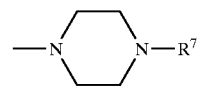

in which

R⁷ denotes hydrogen, methyl or ethyl, which is optionally mono- or disubstituted, in an identical or different manner, by hydroxyl, methoxy or ethoxy, or denotes cyclopentyl or cyclohexyl, and the heterocycles mentioned under R³ and R⁴, formed together with the nitrogen atom, are optionally mono- or disubstituted, in an identical or different manner, if appropriate also geminally, by hydroxyl, methyl or ethyl, R⁵ and R⁶ identically to or differently from one another denote hydrogen, straight-chain or branched alkyl having up to 6 carbon atoms, hydroxyl or straight-chain or branched alkoxy having up to 6 carbon atoms.

According to a particularly preferred embodiment of the present invention, in the case of the reactants and the final product of the process according to the invention R¹ denotes methyl or ethyl, R² denotes n-propyl, R³ and R⁴ identically to or differently from one another denote methyl or ethyl, which are optionally substituted up to two times in an identical or different manner by hydroxyl, or R³ and R⁴, together with the nitrogen atom, form a piperidinyl or morpholinyl ring or a radical of the formula

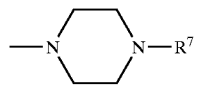

in which

R⁷ denotes hydrogen, methyl or ethyl, which is optionally mono- or disubstituted, in an identical or different manner, by hydroxyl, methoxy or ethoxy, or denotes cyclopentyl or cyclohexyl, and the heterocycles mentioned under R³ and R⁴, formed together with the nitrogen atom, are optionally mono- or disubstituted, in an identical or different manner, if appropriate also geminally, by hydroxyl, methyl or ethyl, R⁵ denotes hydrogen, R⁶ denotes ethoxy.

In the context of the present invention, the substituents, if not stated otherwise, in general have the following meaning:

Alkyl in general represents a straight-chain or branched hydrocarbon radical having 1 to 6 carbon atoms. Examples which may be mentioned are methyl, ethyl, propyl, isopropyl, butyl, isobutyl, pentyl, isopentyl, hexyl, isohexyl.

Alkoxy in general represents a straight-chain or branched hydrocarbon radical having 1 to 6 carbon atoms, which is bonded via an oxygen atom. Examples which may be mentioned are methoxy, ethoxy, propoxy, isopropoxy, butoxy, isobutoxy, pentoxy isopentoxy, hexoxy, isohexoxy. The terms "alkoxy" and "alkyloxy" are used synonymously.

Acyl in general represents straight-chain or branched lower alkyl having 1 to 6 carbon atoms, which is bonded via a carbonyl group. Examples which may be mentioned are: acetyl, ethylcarbonyl, propylcarbonyl, isopropylcarbonyl, butyl-carbonyl and isobutylcarbonyl.

Alkoxycarbonyl can be represented, for example, by the formula

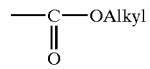

Alkyl here in general represents a straight-chain or branched hydrocarbon radical having 1 to 6 carbon atoms. Examples which may be mentioned are the following alkoxycarbonyl radicals: methoxycarbonyl, ethoxycarbonyl, propoxycarbonyl, iso-propoxycarbonyl, butoxycarbonyl or isobutoxycarbonyl.

Cycloalkyl in general represents a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Halogen in the context of the invention represents fluorine, chlorine, bromine or iodine.

Suitable solvents for the individual steps of the process according to the invention are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine. It is also possible to use mixtures of the solvents mentioned.

Particularly preferably, the reaction of the compounds of the formula (II) with sulphuric acid is carried out without solvent and the subsequent one-pot reaction in the case of the reaction with thionyl chloride is preferably carried out without solvent and in the subsequent reaction with the amine of the formula (IV) in xylene.

The reaction temperature in the process steps according to the invention can in general be varied within a relatively wide range. In general, it is carried out in a range from –20° C. to 200° C., preferably from 0° C. to 70° C.

The process steps according to the invention are generally carried out at normal pressure. However, it is also possible to carry them out at elevated pressure or at reduced pressure (e.g. in a range from 0.5 to 5 bar).

In the first step of the process according to the invention, the sulphuric acid is employed in an excess, for example in a 2- to 2-fold excess, preferably in a 2- to 10-fold excess in each case relative to 1 mol of the compound of the formula (II).

In the second step of the process according to the invention, the thionyl chloride is employed in an excess, for example in a 2- to 20-fold excess, preferably in a 5- to 15-fold excess, in each case relative to 1 mol of the compound of the formula (III). The amine (IV) is employed in an equimolar amount or in an excess, for example in a 2- to 10-fold excess, preferably in a 2- to 5-fold excess, in each case relative to 1 mol of the compound of the formula (III).

The reaction of the compound of the formula (III) with thionyl chloride is preferably carried out in the presence of catalytic amounts of a base, catalytic amounts being understood as meaning a marked (for example at least ten-fold) excess of the base in comparison to the reactants. Suitable bases are, in general, cyclic amines, such as, for example, piperidine, pyridine, 4-N,N-dimethylaminopyridine, or C₁–C₄-alkylamines, such as, for example, triethylamine, or preferably amides such as, for example, N,N-dimethylformamide or N,N-dibutylformamide. N,N-dimethylformamide is particularly preferred.

The compounds of the formula (II) can be prepared, as described in WO 99/24433, from compounds of the formula (V)

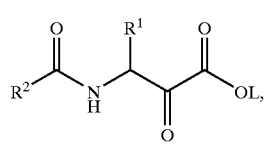

in which
$R^1$ and $R^2$ have the meaning indicated above
and
L represents straight-chain or branched alkyl having up to 4 carbon atoms,
with compounds of the general formula (VI)

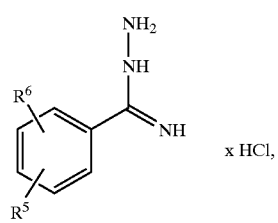

in which
$R^5$ and $R^6$ have the meaning indicated above.

This reaction can either be carried out as described in WO 99/24433 in a two-stage reaction in the system ethanol and phosphorus oxychloride/dichloroethane or preferably according to the present invention in a two-stage reaction as a one-pot process in the systems methanol and phosphorus oxychloride/acetic acid or particularly preferably methanol and acetyl chloride/acetic acid.

Suitable solvents for this reaction are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or alcohols such as methanol, ethanol, n-propanol, isopropanol or n-butanol, or ethyl acetate, acetonitrile, acetone, dimethoxyethane or pyridine or acids such as acetic acid. It is likewise possible to use mixtures of the solvents mentioned. According to the present invention, alcohols, particularly preferably methanol, are preferred for the first step, and either dichloroethane (as described in WO 99/24433) or particularly preferably acetic acid for the second step.

The reaction temperature in this reaction can in general be varied within a relatively wide range. In general, the reaction is carried out in a range from −20° C. to 200° C., preferably from 0° C. to 70° C.

This reaction is in general carried out at normal pressure. However, it is also possible to carry out the reaction at elevated pressure or at reduced pressure (e.g. in a range from 0.5 to 5 bar).

The reactants are employed in this reaction as crude products. Depending on the constitution of the reactants, these can be employed in equimolar amounts or one of the two reactants can be employed in an excess.

The compounds of the formula (V) are known in some cases or can be prepared according to WO 99/24433 by converting compounds of the general formula (VII)

 (VII)

in which
$R^2$ has the meaning indicated above
and
T represents halogen, preferably chlorine, firstly by reaction with compounds of the general formula (VII)

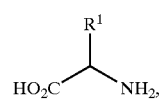 (VIII)

in which
$R^1$ has the meaning indicated above if appropriate in inert solvents, if appropriate in the presence of a base and/or trimethylsilyl chloride, into the compounds of the general formula (IX)

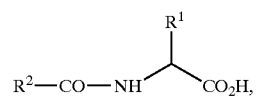 (IX)

in which
$R^1$ and $R^2$ have the meaning indicated above, and finally reacted with the compound of the formula (X)

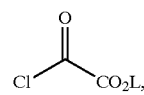 (X)

in which
L has the meaning indicated above, in inert solvents, if appropriate in the presence of a base.

Suitable solvents for the individual steps of the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine. It is also possible to use mixtures of the solvents mentioned.

For the first step, the reaction of the compound of the formula (VII) with the compound of the formula (VII), the carrying-out of the reaction in dichloromethane or the carrying-out of the reaction without inert solvent is particularly preferred, the reaction being carried out in the presence of a base, preferably an alkali metal or alkaline earth metal hydroxide, particularly preferably sodium hydroxide solution as a solvent.

For the second step, the reaction of the compound of the formula (IX) with the compound of the formula (X), the carrying-out of the reaction in a mixture of tetrahydrofuran and pyridine is particularly preferred.

Suitable bases are in general cyclic amines, such as, for example, piperidine, pyridine, dimethylaminopyridine or $C_1$–$C_4$-alkylamines, such as, for example, triethylamine. Triethylamine, pyridine and/or dimethylaminopyridine are preferred.

The base is in general employed in an amount from 1 to 5 mol equivalents, preferably 1 to 3 mol equivalents in comparison to the reactants.

The reaction temperature can in general be varied within a relatively wide range. In general, the reaction is carried out in a range from −20° C. to 200° C., preferably from 0° C. to 100° C.

The compounds of the formulae (VII), (VIII) and (X) are known per se or can be prepared by methods known to the person skilled in the art, for example according to the processes described in WO 99/24433.

Depending on the constitution of the reactants, the compounds of the formulae (VII) and (VIII) are employed in equimolar amounts or one of the two reactants is employed in an excess.

Depending on the constitution of the reactants, the compounds of the formulae (IX) and (X) are employed in equimolar amounts or one of the two reactants is employed in an excess. The compound of the formula (X) is preferably employed in a 1.5- to 5-fold excess.

The compounds of the formula (VI) can be prepared in various ways. For example, they can be prepared according to WO 99/24433 by reacting compounds of the general formula (XI)

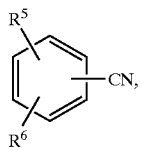

(XI)

in which
$R^5$ and $R^6$ have the meaning indicated above, with ammonium chloride in toluene and in the presence of triethylaluminium in hexane in a temperature range from −20° C. to room temperature, preferably at 0° C. and normal pressure, and the resulting amidine is reacted, if appropriate in situ, with hydrazine hydrate.

The compounds of the general formula (XI) are known per se or can be prepared according to customary methods. For example, according to WO 99/24433, these are accessible from the corresponding phenol derivatives by etherification. Also possible, however, is the reaction of the corresponding benzamides in an inert organic solvent such as toluene with thionyl chloride with heating to, for example, 50–100° C., preferably 70–100° C., to give the compounds of the formula (XI).

Alternatively, the compounds of the formula (VI), however, can also be prepared by reacting the compounds of the formula (XI) in the presence of a base in an inert organic solvent with hydroxylamine hydrochloride to give the compounds of the formula (XII)

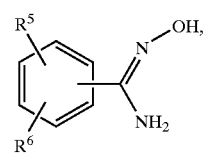

(XII)

in which
$R^5$ and $R^6$ have the meaning indicated above, and then reacting with a reducing agent in an organic solvent to give the compounds of the formula (XIII)

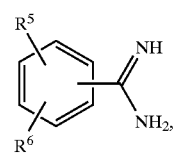

(XIII)

in which
$R^5$ and $R^6$ have the meaning indicated above, which can then be reacted with hydrazine hydrates, if appropriate in situ, to give the compounds of the formula (VI).

Suitable solvents for these reactions are the customary organic solvents which do not change under the reaction conditions. These are preferably alcohols such as methanol, ethanol or iso-propanol, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexaimethylphosphoramide, acetonitrile, acetone, dimethoxyethane or pyridine or acetic acid. It is likewise possible to use mixtures of the solvents mentioned.

The reaction of the compounds of the formula (XI) to give the compounds of the formula (XII) is particularly preferably carried out in isopropanol. The reaction of the compounds of the formula (XII) to give the compounds of the formula (XIII) is particularly preferably carried out in acetic acid. The reaction of the compound of the formula (XIII) with hydrazine hydrate is particularly preferably carried out in methanol.

These reactions are in general carried out at normal pressure. However, it is also possible to work at elevated pressure or at reduced pressure (e.g. in a range from 0.5 to bar).

The reaction temperature can in general be varied within a relatively wide range. In general, the reaction is carried out in a range from −20° C. to 200° C., preferably from 0° C. to 100° C.

The reaction of the compounds of the formula (XI) to give the compounds of the formula (XII) is carried out in the presence of a base. Suitable bases are, in particular, cyclic amines, such as, for example, piperidine, pyridine, dimethylaminopyridine or $C_1$–$C_4$-alkylamines, such as, for example, triethylamine. Triethylamine is preferred. The base is in general employed in an amount from 1 mol to 4 mol, in each case relative to 1 mol of the compound of the formula (XI).

The reduction of the compounds of the formula (XII) to give the compounds of the formula (XIII) can be carried out using the reducing agents customary for reactions of this type under the conditions known to the person skilled in the art. According to the invention, hydrogenation in the presence of a catalyst such as palladium on carbon in acetic acid is preferred.

Depending on the composition of the reactants, the compounds of the formula (XI) and hydroxylamine hydrochloride or the compounds of the formula (XIII) and hydrazine hydrate are employed in equimolar amounts or the hydroxylamine hydrochloride or the hydrazine hydrate is employed in an excess.

The compounds according to the invention are inhibitors of cGMP-metabolizing PDEs and are already described in WO 99/24433.

The present invention is shown in greater detail below with the aid of non-restricting preferred examples and comparison examples. If not stated otherwise, all quantitative data relate to percentages by weight.

EXAMPLES $^1$H-NMR spectra were measured at room temperature using the WP-200 SY spectrometer from Bruker. The solvents used were deuterated dimethyl sulphoxide or deuterochloroform containing tetramethylsilane as an internal standard (if not noted otherwise).

MS spectra were measured using the spectrometers M 40 from AMD and API 150 from PE/SCIEX. The relative signal intensity is indicated (in percent relative to the base peak).

HPLC analytical data were recorded using the HP 1090 apparatus from Hewlett Packard. The exact conditions are indicated in the respective working examples.

Starting Compounds

Example I

Preparation of 2-(2-ethoxyphenyl)-5-methyl-7-propyl-3H-imidazo-[5,1-f][2,4]triazin-4-one Ia) Preparation of 2-butyrylaminopropionic acid

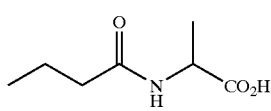

A solution of 100 kg of D,L-alanine in aqueous sodium hydroxide solution is reacted in the cold with 119 kg of butyryl chloride. After addition of butyl acetate, the mixture is acidified with hydrochloric acid, the organic phase is separated off and the aqueous phase is re-extracted. The organic phase is dried by azeotropic distillation. The crystallizate is isolated, washed with butyl acetate and dried.

Yield: 132.6 kg (68%)

$^1$H-NMR: δ=0.8 (t, 3H), 1.25 (d, 3H), 1.5 (m, 2H), 2.1 (t, 2H), 4.2 (q, 1H), 8.1 (d, NH), 12.0–12.7 (s, COOH)

MS: 336 (2M+$NH_4$, 40), 319 (2M+H, 15), 177 (M+$NH_4$, 100), 160 (M+H, 20)

Ib) Preparation of 2-ethoxybenzonitrile

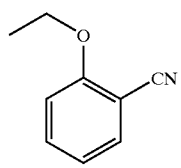

260 kg of thionyl chloride are added at 85–95° C. to a suspension of 250 kg of 2-ethoxybenzamide in toluene under metering control. The reaction mixture is stirred in the presence of heat. Thionyl chloride and toluene are then distilled off in vacuo. The product is employed in the subsequent stage as a crude product.

Yield: 228.5 kg (crude product)

$^1$H-NMR: δ=1.45 (t, 3H), 4.15 (q, 2H), 7.0 (m, 2H, phenyl), 7.5 (m, 2H, phenyl)

MS: 312 (2M+$N_4$, 35), 165 (M+$NH_4$, 100), 147 (5)

Ic) Preparation of 2-ethoxy-N-hydroxybenzamidine

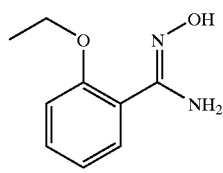

111 kg of 2-ethoxybenzonitrile (crude product) from Example Ib are heated under reflux with 164 l of triethylamine and 73 kg of hydroxylamine hydrochloride in isopropanol. The reaction mixture is treated with water and cooled. The crystallizate is isolated, washed and employed in the subsequent stage as a moist product.

Yield: 92.6 kg (moist product)

$^1$H-NMR: δ=1.35 (t, 3H), 4.1 (q, 2H), 5.6 (s, 2H), 6.9–7.4 (4H, phenyl), 9.4 (s, 1H, OH)

MS: 361 (2M+H, 30), 198 (M+$NH_4$, 30), 181 (M+H, 100)

Id) Preparation of 2-ethoxybenzamidine hydrochloride

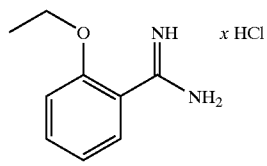

135 kg of 2-ethoxy-N-hydroxybenzamidine (moist product) from Example Ic are hydrogenated at 50–60° C. in acetic acid using palladium on carbon as a catalyst. For the work-up, the hydrogenation reaction is freed from the catalyst, treated with hydrochloric acid and concentrated.

Residual acetic acid and water are removed by azeotropic distillation with toluene. The crystallizate is isolated and dried in vacuo.

Yield: 136.4 kg

H-NMR: 1.35 (t, 3H), 4.15 (q, 2H), 7.1–7.7 (m, 4H, phenyl), 9.1–9.4 (2×s, 3H), 10.5–10.7 (s, 1H)

MS: 329 (2M+H, 10), 165 (M+H, 100)

Ie) Preparation of 2-(2-ethoxyphenyl)-5-methyl-7-propyl-3H-imidazo[5,1-f][1,2,4]-triazin-4-one

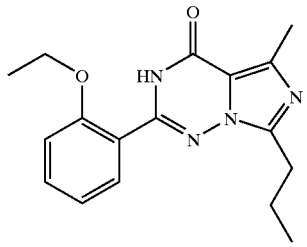

231 kg of 2-butyrylaminopropionic acid from Example Ia are treated in tetrahydrofuran with 341 kg of pyridine, catalytic amounts of 4-N,N-dimethylaminopyridine and 392 kg of ethyl chloroxalate and stirred with heating under reflux. The reaction mixture is taken up in ethyl acetate, washed with water and the ethyl acetate phase is concentrated. The distillation residue is taken up in methanol and reacted with the following solution.

192 kg of 2-ethoxybenzamidine hydrochloride from Example Id are treated in methanol with 47.5 kg of hydrazine hydrate and the mixture is stirred at room temperature. The solution is combined with the solution of 2-butyrylamino-1-ethoxycarbonylpropenyl ethyl oxalate prepared above. The reaction mixture thus obtained is stirred with heating under reflux. Methanol is removed by distillation and replaced by acetic acid.

Option A:

138.6 kg of phosphorus oxychloride are added and stirred in the presence of heat. Acetic acid is distilled off in vacuo. The residue is treated with water and dichloromethane or optionally methyl isobutyl ketone and rendered neutral using sodium hydroxide solution. The organic phase is concentrated, and the residue is dissolved in acetone and crystallized with cooling. The crystallizate is isolated, washed and dried.

Option B:

At least 190 kg of acetyl chloride are added and stirred in the presence of heat. Acetic acid is distilled off in vacuo. The distillation residue is treated with acetone and water, and the product is crystallized by rendering neutral with sodium hydroxide solution. The product is isolated, washed and dried.

Yield: 90–160 kg $^1$H-NMR: δ=1.0 (t, 3H), 1.6 (t, 3H), 1.9 (m, 2H), 2.8 (s, 3H), 3.3 (t, 2H), 4.3 (q, 2H), 7.0–8.2 (Ar, 4H), 10.3 (CONH, 1H)

MS: 313 (M+H, 100), 149 (25), 151 (40), 121 (15)

HPLC: Kromasil C-18 phase, neutral phosphate buffer, acetonitrile, 233 nm, linear gradient of 30% acetonitrile→80% acetonitrile (30 min.): 99 area % ($R_t$ 19.1)

PREPARATION EXAMPLES

Example 1a 4-ethoxy-3-(5-methyl-4-oxo-7-propyl-3,4-dihydroimidazo[5,1-f]-[1,2,4]triazin-2-yl)benzenesulphonic acid

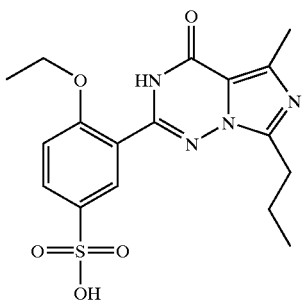

194 kg of 2-(2-ethoxyphenyl)-5-methyl-7-propyl-3H-imidazo[5,1-f][1,2,4]triazin-4-one from Example Ie are reacted with 504 kg of concentrated sulphuric acid. The reaction mixture is added to water, cooled, and the crystallizate is isolated and dried in vacuo.

Yield: 195.2 kg $^1$H-NMR: δ=0.95 (t, 3H), 1.3 (t, 3H), 1.8 (m, 2H), 2.6 (s, 3H), 3.05 (t, 2H), 4.1 (q, 2H), 7.15 (Ar, 1H), 7.75 (m, 2H), 12.3 (SO$_2$OH)

MS: 393 (M+H, 100), 365 (25), 151 (40)

HPLC: X-Terra C-18 phase, aqueous phosphoric acid, acetonitrile, 242 nm, linear gradient of 10% acetonitrile→90% acetonitrile (20 min.): 98 area % ($R_t$ 9.2)

Example 1b

2-[2-ethoxy-5-(4-ethlylpiperazin-1-sulphonyl)phenyl]-5-methyl-7-propyl-3H-imidazo[5,1-f][1,2,4]triazin-4-one

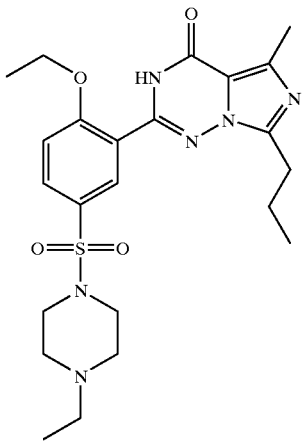

22.5 kg of 4-ethoxy-3-(5-methyl-4-oxo-7-propyl-3,4-dihydro-imidazo[5,1-f][1,2,4]-triazin-2-yl)benzenesulphonic acid from Example 1a are reacted with 74 kg of thionyl chloride and catalytic amounts of dimethylformamide until the evolution of gas has ended. Xylene is repeatedly added to the reaction mixture and thionyl chloride is distilled off. 15.1 kg of N-ethylpiperazine are added to the suspension and it is stirred. After the addition of water, it is adjusted to pH 1 using hydrochloric acid, and the phases are separated. The aqueous phase is treated with acetone and rendered neutral by addition of sodium hydroxide solution. The mixture is cooled, and the crystallizate is isolated, washed and dried in vacuo.

Yield: 26.1 kg $^1$H-NMR: δ=1.0 (2×t, 6H), 1.6 (t, 3H), 1.9 (m, 2H), 2.45 (q, 2H), 2.55 (m, 4H), 2.65 (s, 3H), 3.0 (t, 2H), 3.1 (m, 4H), 4.35 (q, 2H), 7.15 (Ar, 1H), 7.9 (Ar, 1H), 8.4 (Ar, 1H), 9.8 (CONH)

MS: 489 (M+H, 100), 345 (10), 313, (10), 285 (10), 113 (20)

HPLC: X-Terra C-18 phase, neutral phosphate buffer, acetonitrile, 242 nm, linear gradient of 20% acetonitrile→75% acetonitrile (20 min.): 98 area % ($R_t$ 16.3)

1c) 2-[2-ethoxy-5-(4-ethylpiperazin-1-sulphonyl)phenyl]-5-methyl-7-propyl-3H-imidazo[5,1-f][1,2,4]triazin-4-one hydrochloride trihydrate

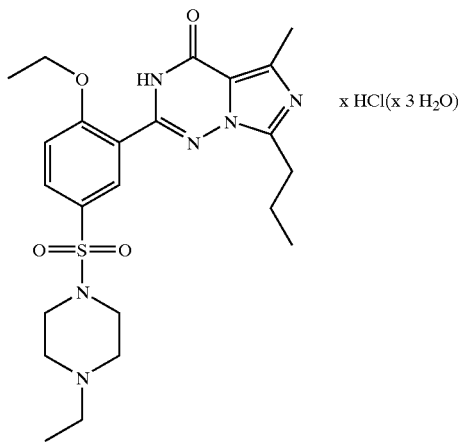

x HCl(x 3 H$_2$O)

22.5 kg of 2-[2-ethoxy-5-(4-ethylpiperazin-1-sulphonyl)phenyl]-5-methyl-7-propyl-3H-imidazo[5,1-f][1,2,4]triazin-4-one from Example 1b are dissolved in 5.1 kg of concentrated hydrochloric acid and acetone/water (12:1 v/v) in the presence of heat. The clear solution is filtered hot and crystallized by cooling and seeding. The crystallizate is isolated, washed and dried in vacuo at about 30° C. and about 300 mbar.

Yield: 25.4 kg

M.p. (DSC): 192° C.

HPLC: X-Terra C-18 phase, neutral phosphate buffer, acetonitrile, 242 nm, linear gradient of 20% acetonitrile→75% acetonitrile (20 min.): 99 area % ($R_t$ 16.3)

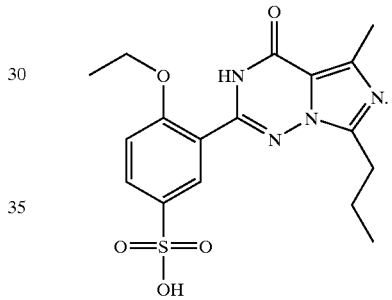

The invention claimed is:

1. A compound 4-ethoxy-3-(5-methyl-4-oxo-7-propyl-3,4-dihydroimidazol[5,1-fl-[1,2,4]triazin-2-yl)benzenesulphonic acid